United States Patent
Iwashita et al.

(10) Patent No.: US 10,698,122 B2
(45) Date of Patent: Jun. 30, 2020

(54) RADIATION IMAGING SYSTEM, SIGNAL PROCESSING APPARATUS, AND, RADIOGRAPHIC IMAGE SIGNAL PROCESSING METHOD

(71) Applicant: CANON KABUSHIKI KAISHA, Tokyo (JP)

(72) Inventors: Atsushi Iwashita, Tokyo (JP); Sho Sato, Tokyo (JP); Kosuke Terui, Yokohama (JP); Yoshiaki Ishii, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 147 days.

(21) Appl. No.: 15/771,990

(22) PCT Filed: Oct. 24, 2016

(86) PCT No.: PCT/JP2016/004669
§ 371 (c)(1),
(2) Date: Apr. 27, 2018

(87) PCT Pub. No.: WO2017/073041
PCT Pub. Date: May 4, 2017

(65) Prior Publication Data
US 2018/0341029 A1    Nov. 29, 2018

(30) Foreign Application Priority Data
Oct. 30, 2015 (JP) .................. 2015-214987

(51) Int. Cl.
*G01T 1/208* (2006.01)
*G01N 23/04* (2018.01)
(Continued)

(52) U.S. Cl.
CPC .......... *G01T 1/208* (2013.01); *A61B 6/4233* (2013.01); *A61B 6/4241* (2013.01);
(Continued)

(58) Field of Classification Search
CPC .. G01T 1/208; G01T 1/20; G01T 1/17; G01T 1/36; G01T 1/2018; G01N 23/04; A61B 6/4241; A61B 6/4233
See application file for complete search history.

(56) References Cited

U.S. PATENT DOCUMENTS

2009/0296884 A1    12/2009   Honda
2015/0279027 A1*   10/2015   Nagai ................. G06T 5/00
                                                  382/132

FOREIGN PATENT DOCUMENTS

JP    2009-285356 A    12/2009
JP    2011-19591 A      2/2011
WO    02/058558 A2      8/2002

* cited by examiner

*Primary Examiner* — Michael C Bryant
(74) *Attorney, Agent, or Firm* — Canon U.S.A., Inc. IP Division

(57) ABSTRACT

In order to provide a large-area radiation imaging apparatus that has an energy resolution while suppressing the occurrence of an artifact, the radiation imaging apparatus includes a detector and a signal processing unit. The detector includes a plurality of pixels for acquiring a pixel value in accordance with incident radiation. The signal processing unit performs signal processing for estimating energy of a radiation quantum of the incident radiation at a predetermined pixel included in the pixels using the amount of change in the pixel value of the predetermined pixel.

18 Claims, 11 Drawing Sheets

(51) Int. Cl.
*A61B 6/00* (2006.01)
*G01T 1/36* (2006.01)
*G01T 1/17* (2006.01)
*G01T 1/20* (2006.01)

(52) U.S. Cl.
CPC ........... *A61B 6/5258* (2013.01); *G01N 23/04* (2013.01); *G01T 1/17* (2013.01); *G01T 1/20* (2013.01); *G01T 1/2018* (2013.01); *G01T 1/36* (2013.01)

[Fig. 1]
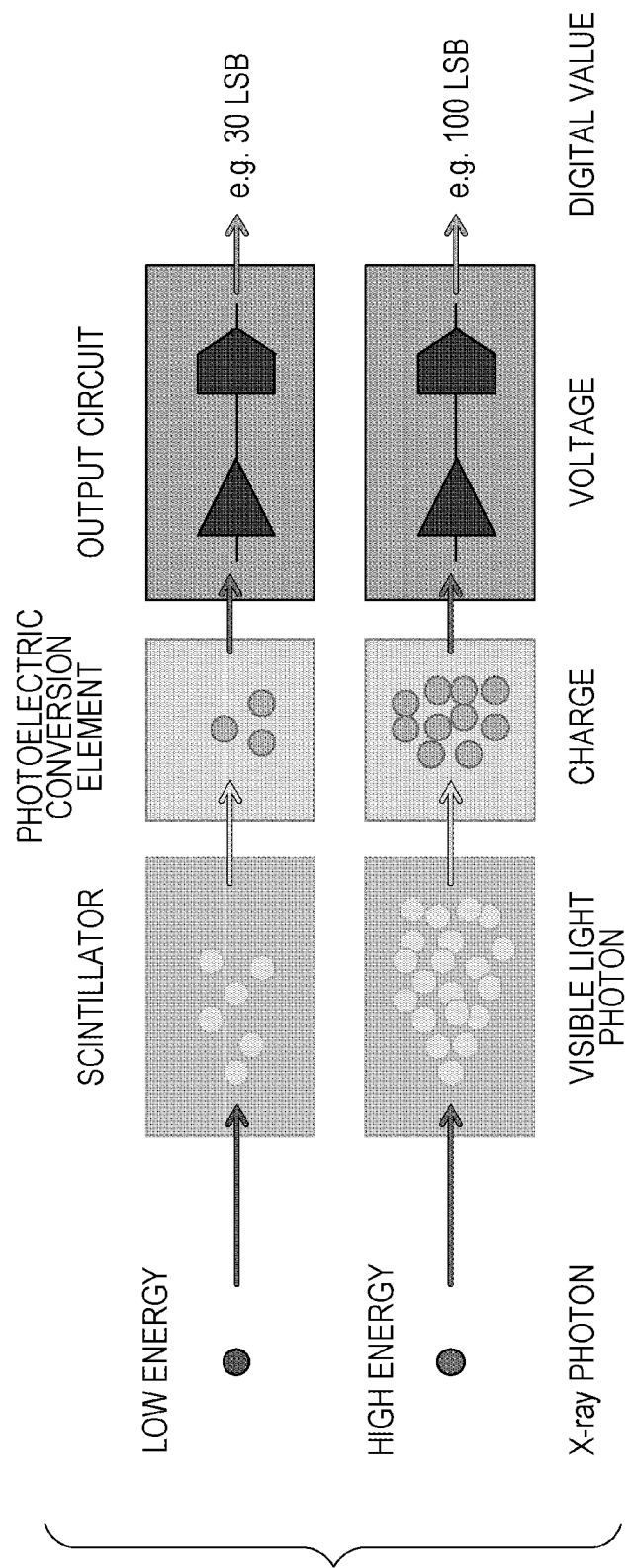

[Fig. 2]
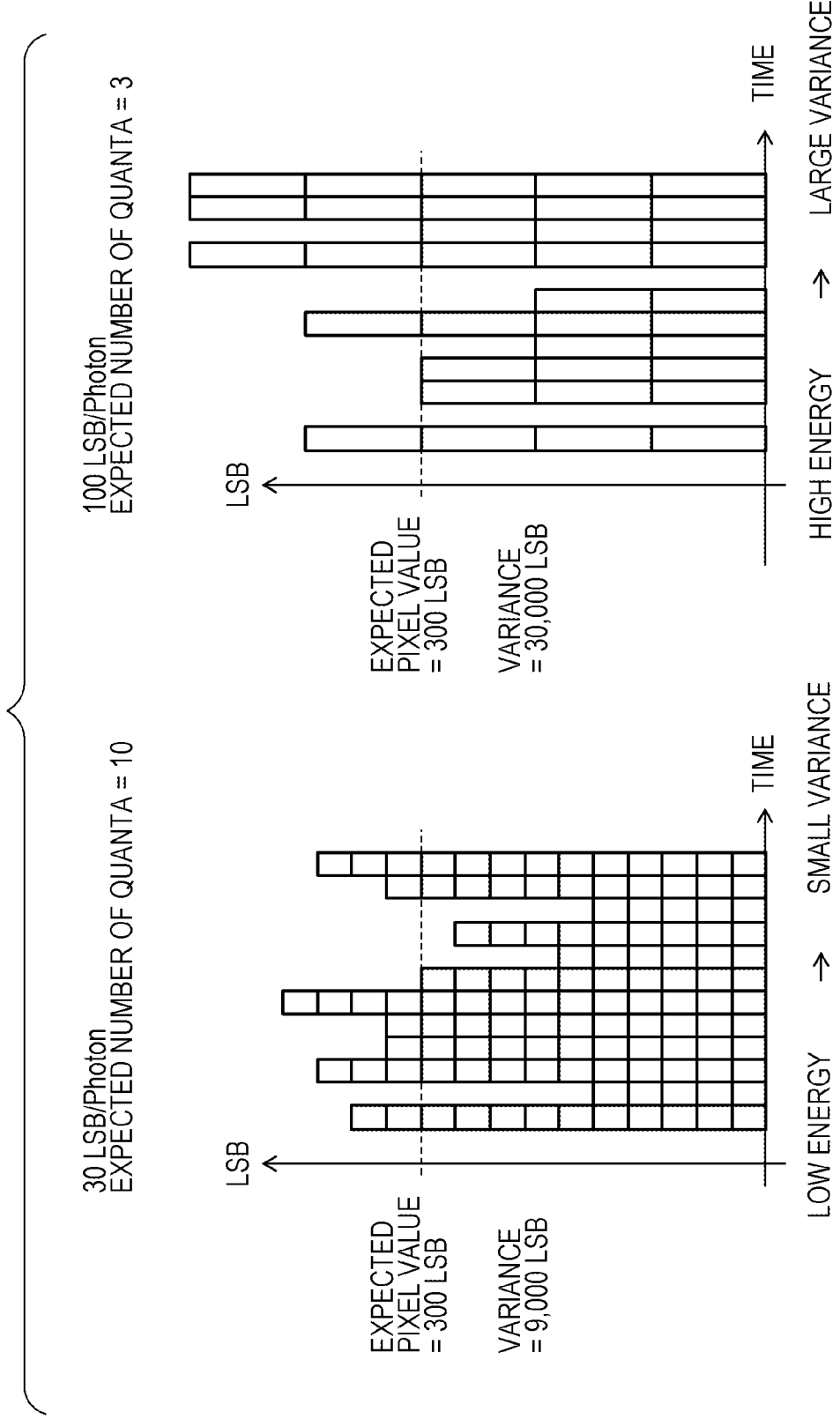

[Fig. 3A]
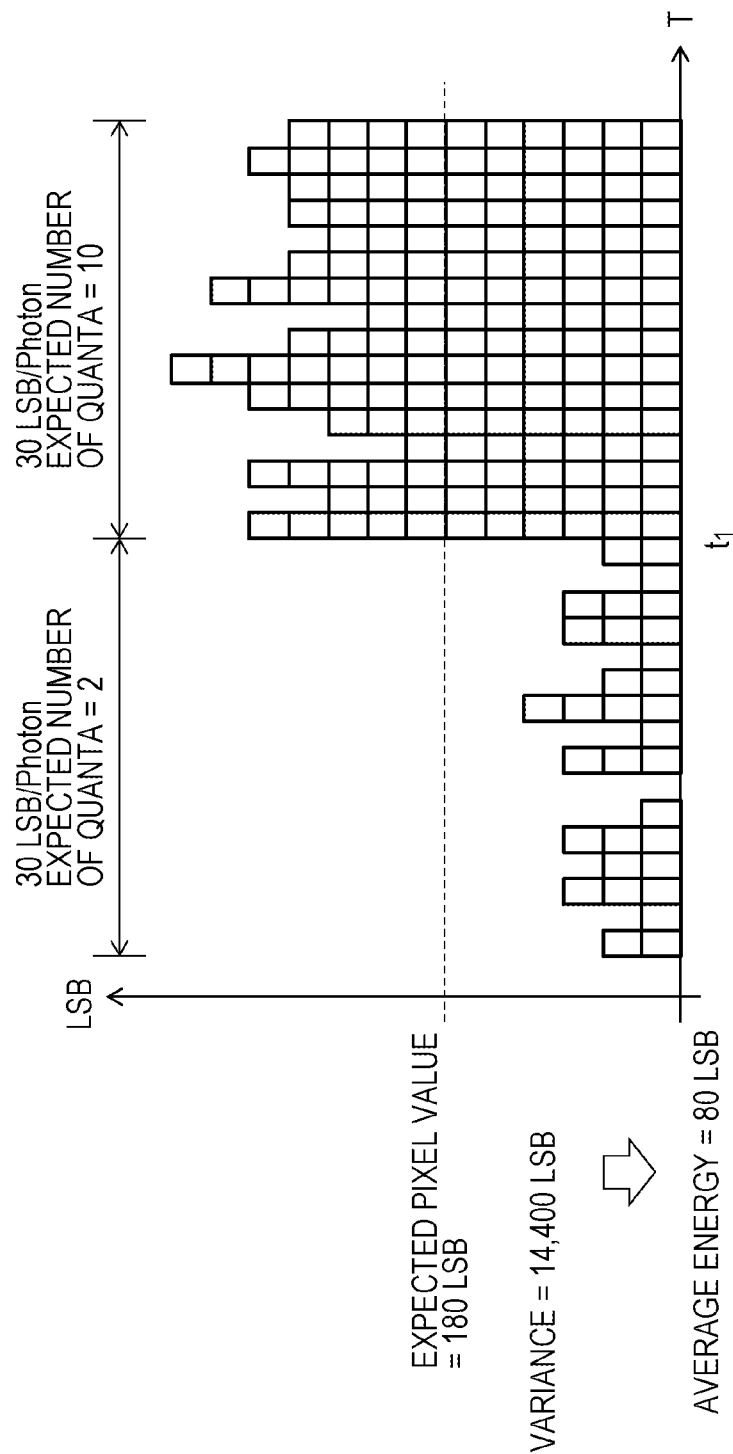

[Fig. 3B]
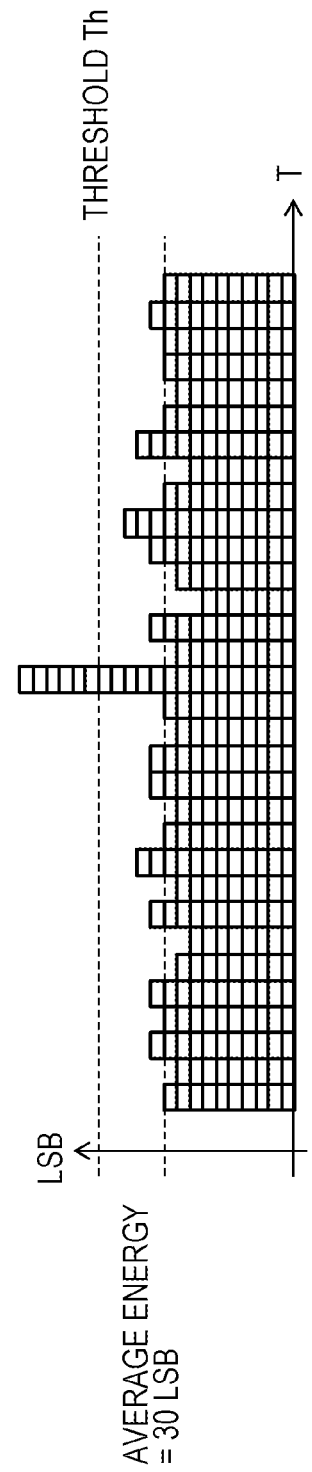

[Fig. 4A]
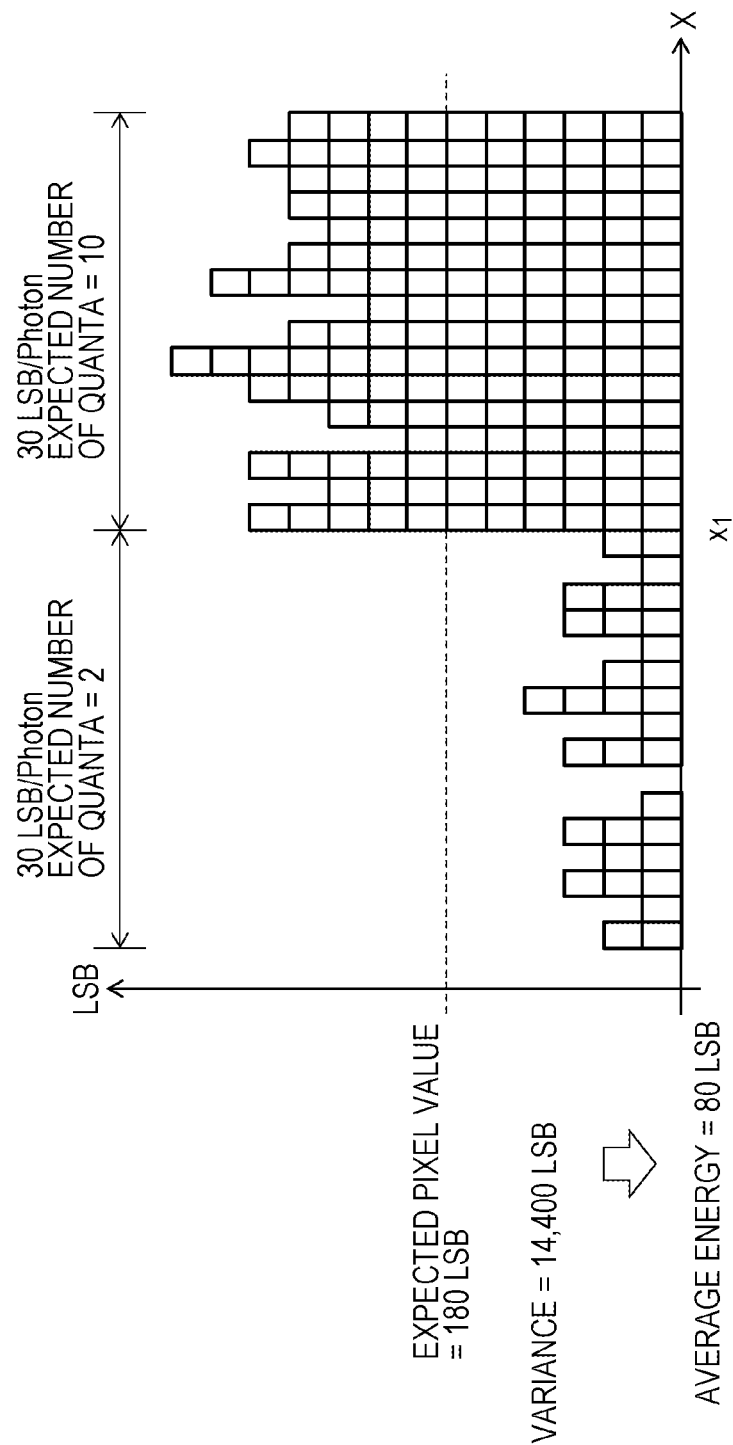

[Fig. 4B]
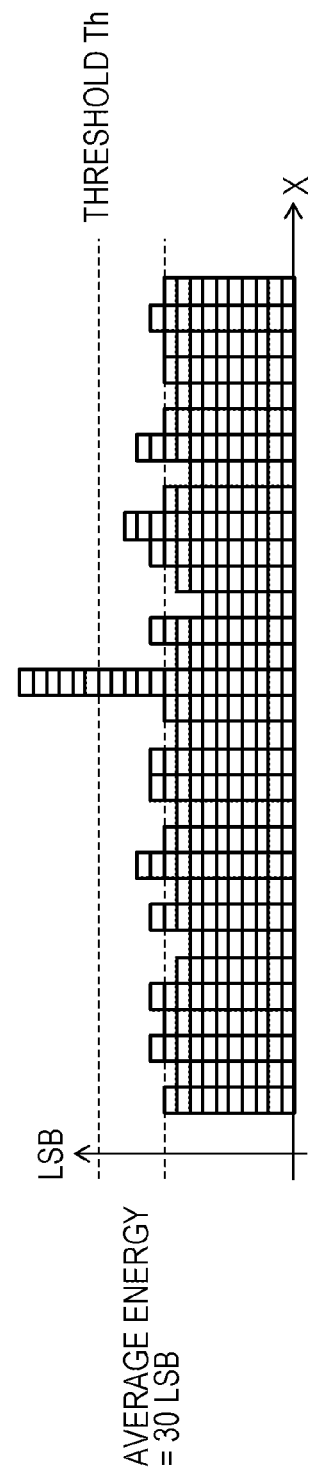

[Fig. 5]
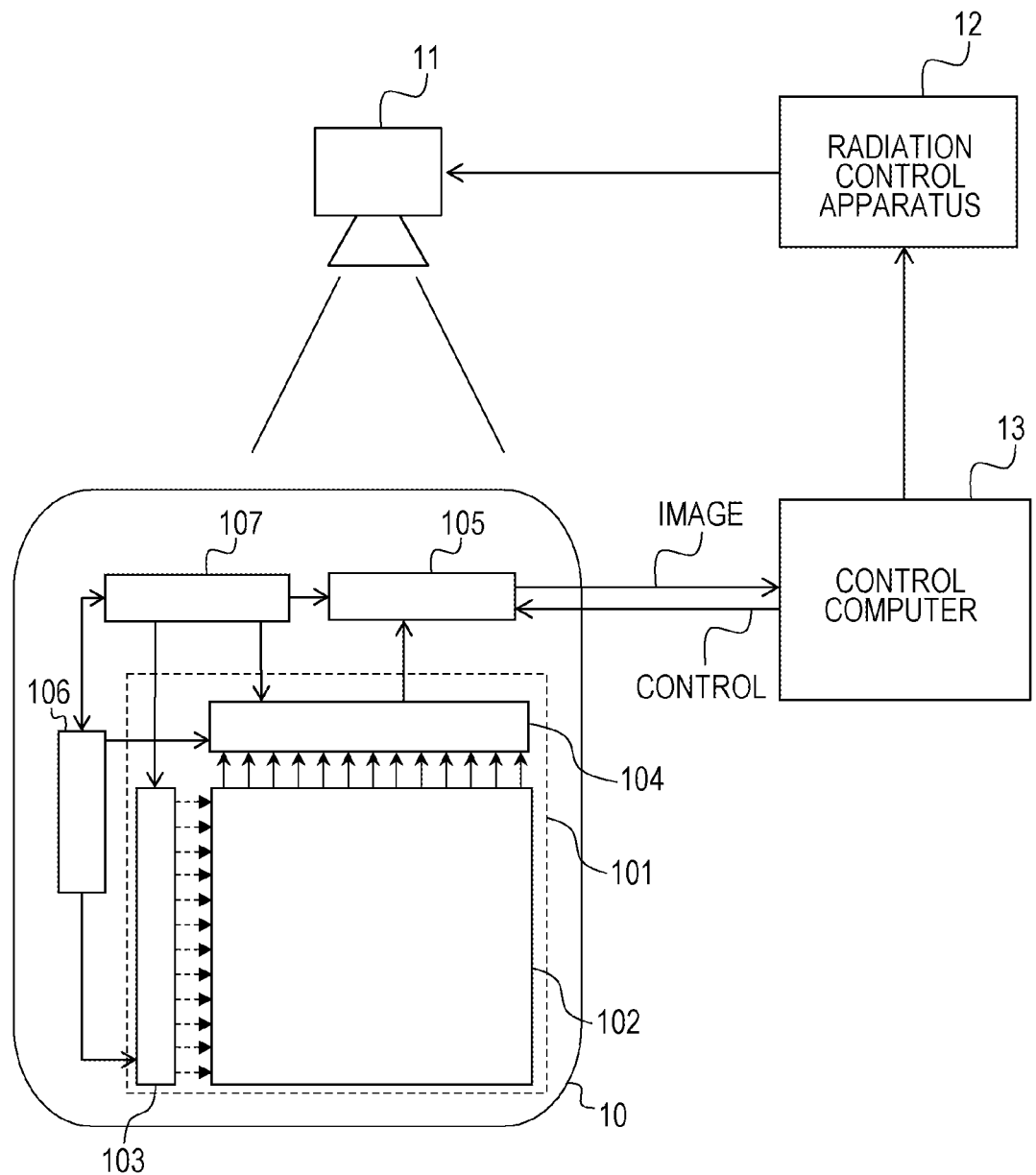

[Fig. 6A]
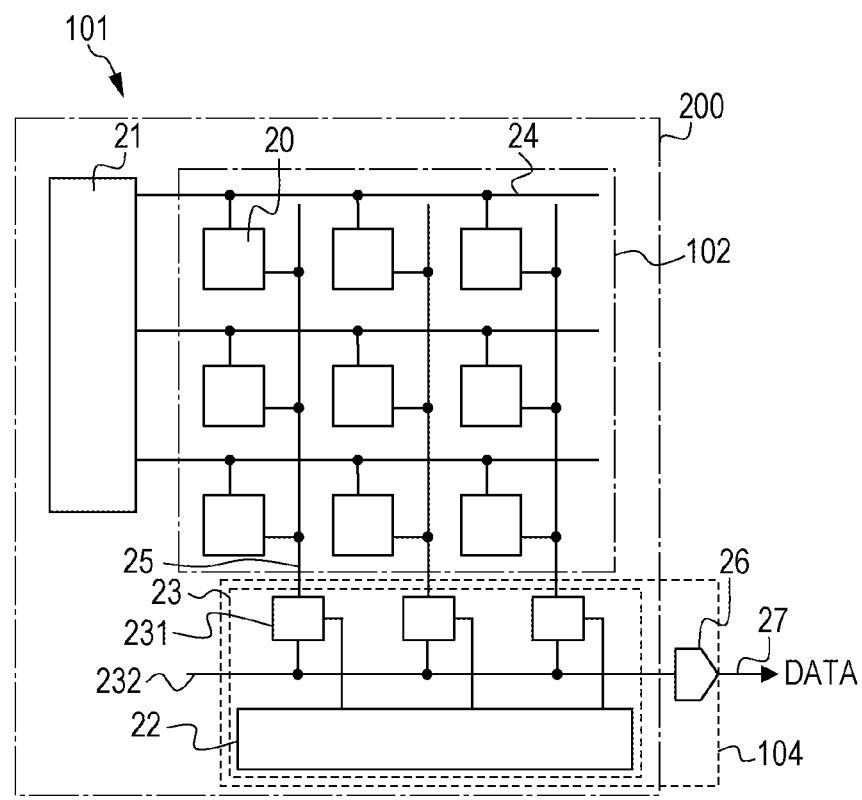

[Fig. 6B]
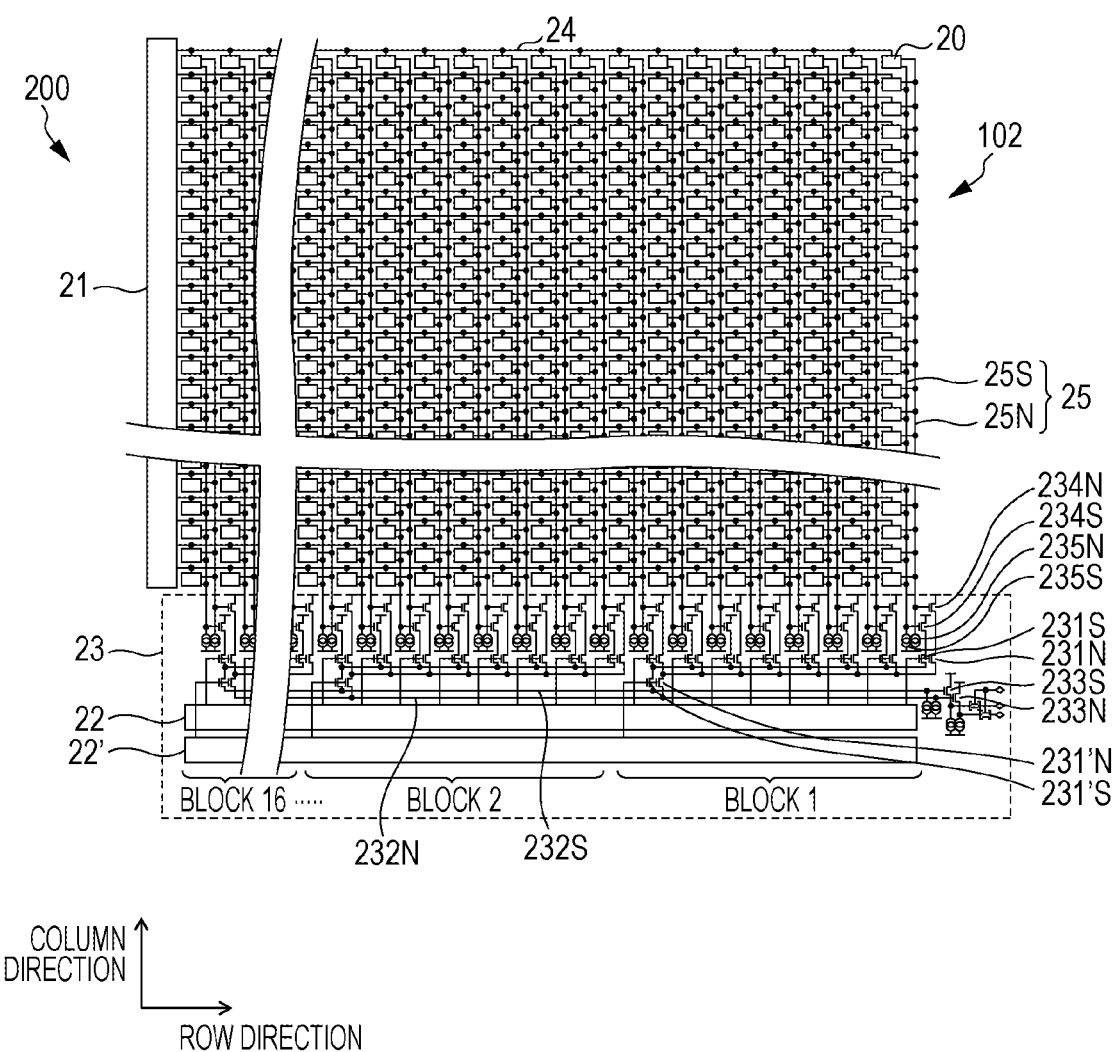

[Fig. 7]
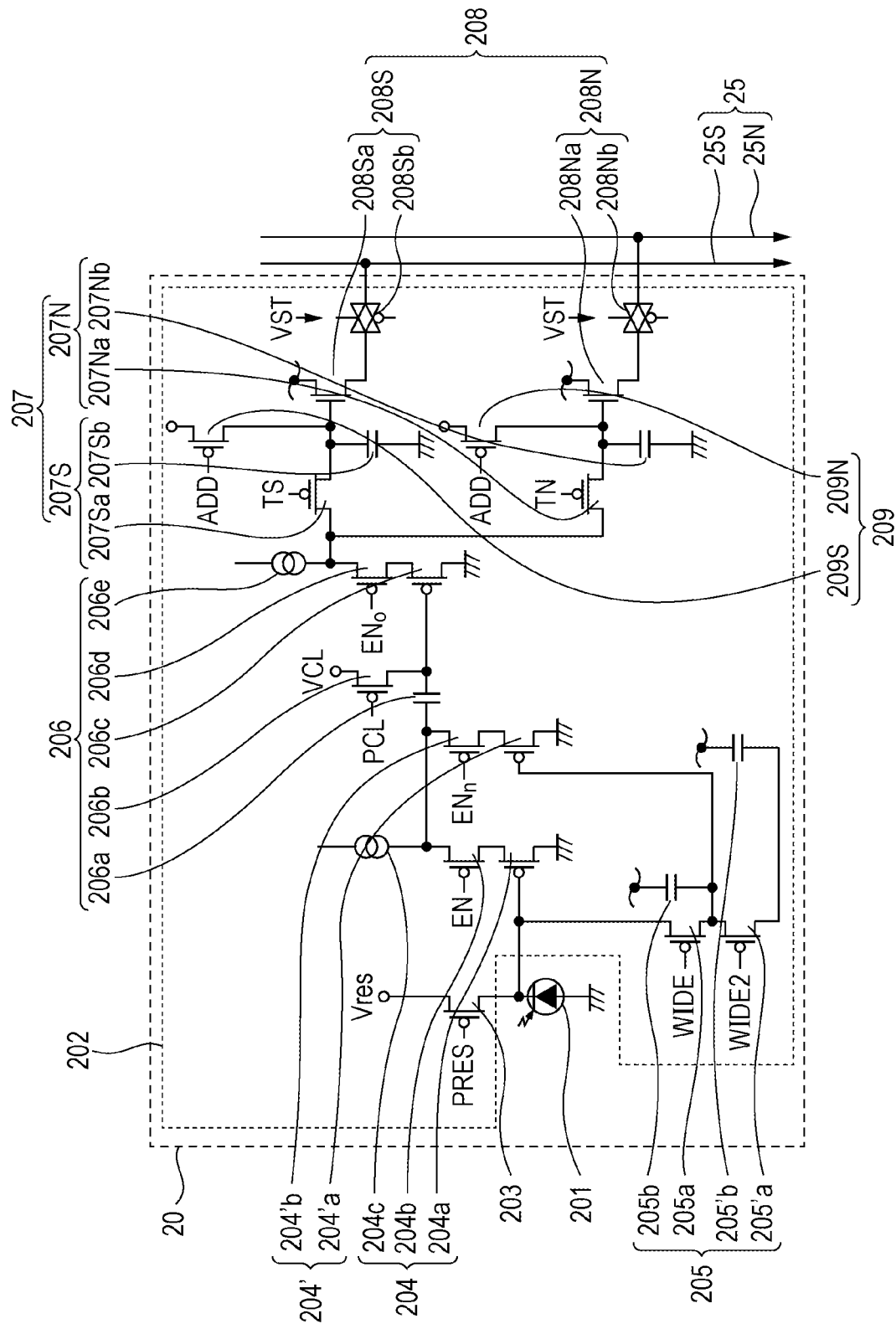

[Fig. 8]
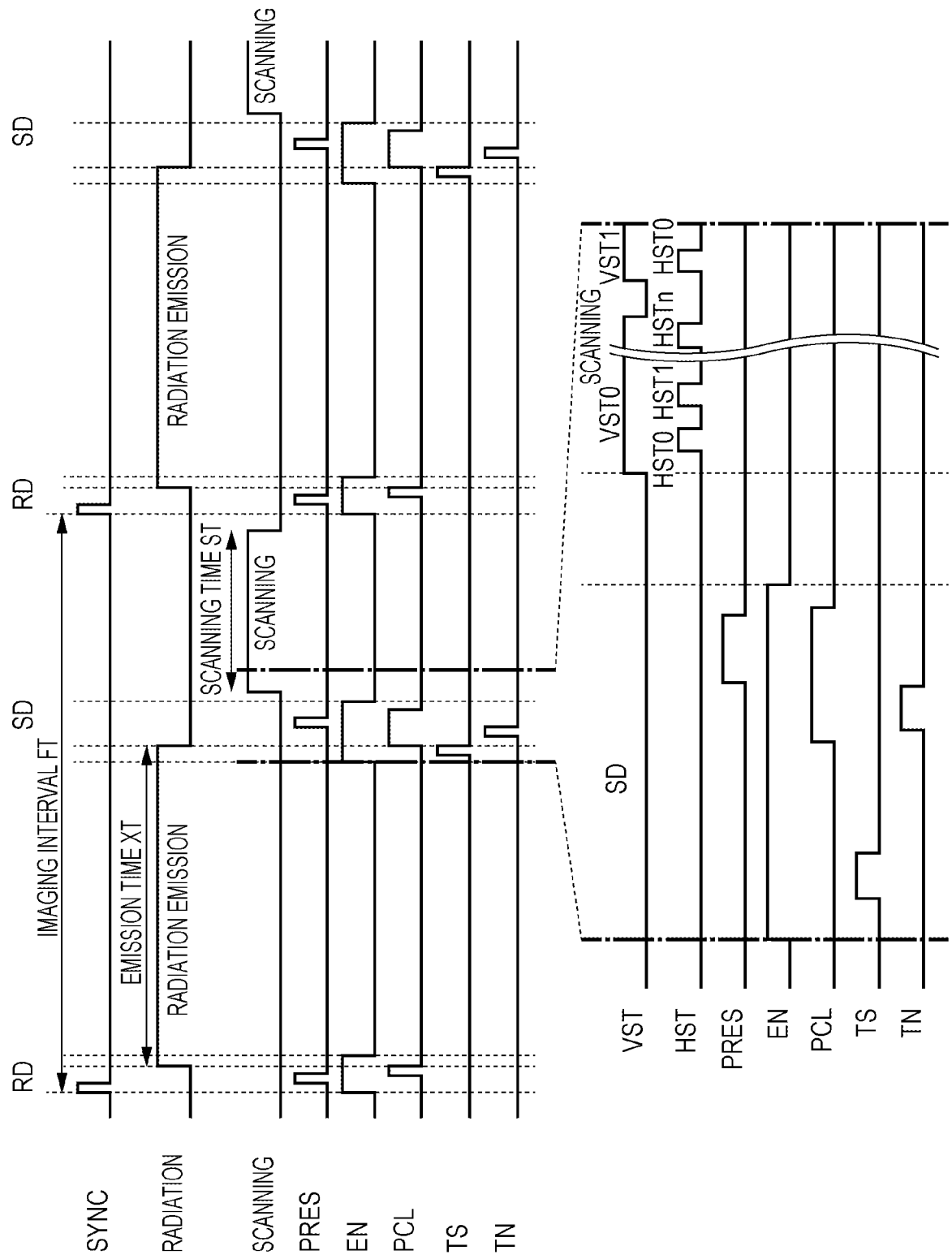

RADIATION IMAGING SYSTEM, SIGNAL PROCESSING APPARATUS, AND, RADIOGRAPHIC IMAGE SIGNAL PROCESSING METHOD

TECHNICAL FIELD

The present invention relates to a radiation imaging system, a signal processing apparatus, and a radiographic image signal processing method which are applied in, for example, medical image diagnosis apparatuses, nondestructive inspection apparatuses, and radiological analysis apparatuses.

BACKGROUND ART

Radiation imaging apparatuses using a planar detector (hereinafter referred to as a Flat Panel Detector (FPD)) made of a semiconductor material are known as imaging apparatuses used for a medical image diagnosis or a nondestructive inspection using radiation (X-ray). In, for example, a medical image diagnosis, such a radiation imaging apparatus can be used as a digital imaging apparatus for capturing a still image or a moving image.

Examples of an FPD include an integral-type sensor and a photon counting-type sensor. Integral-type sensors measure the total amount of charge generated by incidence of radiation. On the other hand, photon counting-type sensors distinguish the energy (wavelength) of incident radiation and count the number of detections of radiation for each of a plurality of energy levels. That is, since photon counting-type sensors have an energy resolution, they can improve a diagnostic capability as compared with integral-type sensors. However, since the number of incident radiation quanta is enormous, a high operation speed is needed for the count of these radiation quanta. It has been therefore difficult to realize a large-area FPD with a photon counting-type sensor.

PTL 1 discloses a radiation imaging apparatus that has an energy resolution by estimating, for each predetermined region, the number of radiation quanta and an average energy using information about an average image density and information about the variance of image density. Using the technique disclosed in PTL 1, a sensor having an energy resolution can be realized even if the operation speed of the sensor is lower than that of a photon counting-type sensor.

CITATION LIST

Patent Literature

PTL 1: Japanese Patent Laid-Open No. 2009-285356

SUMMARY OF INVENTION

Technical Problem

However, in the radiation imaging apparatus disclosed in PTL 1, in a case where an image density rapidly changes in a region, large errors occur in the estimated number of radiation quanta and the estimated average energy. As a result, an artifact occurs at, for example, a portion in the region where the edges of a subject overlap or a portion in the region where the subject has moved. This results in the reduction in a diagnostic capability.

The present invention provides a radiation imaging system including a large-area radiation imaging apparatus that has an energy resolution while suppressing the occurrence of an artifact, a radiographic image signal processing apparatus, and a radiographic image signal processing method.

Solution to Problem

A radiation imaging system according to an embodiment of the present invention includes a detector and a signal processor. The detector includes a plurality of pixels from which pixel values based on incident radiation are acquired. The signal processor is configured to perform signal processing for estimating energy of a radiation quantum of the radiation at a predetermined pixel included in the pixels using an amount of change in a pixel value of the predetermined pixel.

Advantageous Effects of Invention

According to an embodiment of the present invention, it is possible to provide a radiation imaging system including a large-area radiation imaging apparatus that has an energy resolution while suppressing the occurrence of an artifact, a radiographic image signal processing apparatus, and a radiographic image signal processing method.

Further features of the present invention will become apparent from the following description of exemplary embodiments with reference to the attached drawings.

BRIEF DESCRIPTION OF DRAWINGS

FIG. 1 is a conceptual diagram describing the concept of the present invention.

FIG. 2 is a conceptual diagram describing the principle of the present invention.

FIG. 3A is a conceptual diagram describing the principle of the present invention.

FIG. 3B is a conceptual diagram describing the principle of the present invention.

FIG. 4A is a conceptual diagram describing the principle of the present invention.

FIG. 4B is a conceptual diagram describing the principle of the present invention.

FIG. 5 is a schematic block diagram of a radiation imaging system.

FIG. 6A is a schematic block diagram describing the configuration of a radiation imaging apparatus.

FIG. 6B is a schematic block diagram describing the configuration of a radiation imaging apparatus.

FIG. 7 is a schematic equivalent circuit diagram of an exemplary single pixel in a radiation imaging apparatus.

FIG. 8 is a timing chart describing an exemplary operation of a radiation imaging apparatus.

DESCRIPTION OF EMBODIMENTS

Embodiments of the present invention will be described in detail below with reference to the accompanying drawings. Radiation is typically an X-ray, but may be an α-ray, a β-ray, or a γ-ray.

The principle of the present invention will be described with reference to FIGS. 1 to 4B. First, the relationship between the energy of a radiation quantum and the output of a radiation imaging apparatus will be described with reference to FIG. 1. FIG. 1 is a conceptual diagram describing the relationship between the energy of X-ray photons that are examples of radiation quanta and the output of a certain radiation imaging apparatus.

The radiation imaging apparatus illustrated in FIG. 1 includes a scintillator for converting X-ray photons into visible light photons, a photoelectric conversion element for converting the visible light photons into charges, and an output circuit for converting a voltage converted from the charges into a digital signal and outputting the digital signal. When X-ray photons that are examples of radiation quanta are absorbed by the scintillator, visible light photons are generated. The number of generated visible light photons changes in accordance with the energy of X-ray photons absorbed by the scintillator. More specifically, the larger the energy of X-ray photons, the larger the number of visible light photons generated in the scintillator. The amount of charge corresponding to the number of charges generated in the photoelectric conversion element is determined in accordance with the number of visible light photons absorbed by the photoelectric conversion element. The amount of charge is converted into an analog voltage value. The analog voltage value is subjected to analog-to-digital conversion, so that the value of a digital signal output from the radiation imaging apparatus is determined. For example, the value of a digital signal output in accordance with X-ray photons having certain energy is 30 LSB, and the value of a digital signal output in accordance with X-ray photons having larger energy is 100 LSB. Accordingly, by acquiring a digital signal corresponding to the amount of charge generated in the photoelectric conversion element each time a single X-ray photon is absorbed by the scintillator, the energy of the X-ray photon can be discriminated on the basis of the value of the digital signal. In this specification, "LSB" is used as a quantization unit in analog-to-digital conversion. For example, 30 LSB means that the number of quantization units is 30.

However, in a radiation imaging apparatus including a large-area FPD used for medical image diagnosis, since the FPD needs to have a high operation speed to count an enormous number of incident radiation quanta, it is difficult to count the number of radiation quanta one by one. In order to overcome this difficulty, a method is considered of estimating the average energy of a plurality of incident radiation quanta in a predetermined period on the basis of the values of digital signals output in the period and estimating the energy of each of the radiation particles on the basis of a result of the estimation.

Next, the principle of estimating the average energy of radiation quanta will be described with reference to FIG. 2. FIG. 2 is a conceptual diagram describing the principle of estimating the average energy of radiation quanta. A plurality of digital image signals are obtained by emitting radiation to a radiation imaging apparatus via a subject for a predetermined period and repeating this emission a plurality of times. It is assumed that the level of radiation emitted for the predetermined period is constant and the subject does not move. Among the obtained digital image signals, digital image signals (hereinafter referred to as pixel values) obtained from a pixel selected from among a plurality of pixels are illustrated in FIG. 2 on a time-series basis. Under the above-described assumption, the pixel values should be constant. However, as illustrated in FIG. 2, there are variations in the time-series pixel values in reality. The variations include quantization noise. The variations may include noise (system noise) of an electronic circuit included in, for example, the output circuit. Since the system noise is very small as compared with the quantization noise, the system noise will be ignored below for the simplification of descriptions.

The quantization noise is generated because of variations in the number of radiation quanta (for example, the number of X-ray photons) per unit time. If the variations in the number of radiation quanta are considered as a probability of occurrence of discrete events per unit time, the variations in the number of radiation quanta conform to the Poisson distribution that is a discrete probability distribution having a specific random variable that counts the number of discrete events occurring at predetermined time intervals. In the Poisson distribution, when a random variable that is a natural number satisfies desired conditions with respect to a constant $\lambda > 0$, it is said that the random variable conforms to the Poisson distribution of the parameter $\lambda$.

For example, in a case where the expected number of radiation quanta emitted to a single pixel per unit time is 10, the variations (e.g. 12, 5, 13, and 11) in the number of radiation quanta emitted to the pixel per unit time occur in reality. If the value of a digital signal output in accordance with a single radiation quantum having certain energy is 30 LSB as described previously, the variations (e.g. 360 LSB, 150 LSB, 390 LSB, and 330 LSB) in a pixel value occur in reality. If the number of samples that is the number of acquired pixel values is infinitely increased, the expected pixel value becomes 300 LSB and variations (hereinafter referred to as a variance) become 9.000 LSB.

For example, a case will be considered where the expected number of radiation quanta emitted to a single pixel per unit time is 3 and the value of a digital signal output in accordance with a single radiation quantum having certain energy is 100 LSB. In this case, if the number of samples is infinitely increased, the expected pixel value becomes 300 LSB and variations (hereinafter referred to as a variance) become 30,000 LSB.

That is, an image formed of radiation quanta having larger energy has a larger variance of pixel values regardless of whether an average pixel value is constant. Using this feature, the energy of a radiation quantum such as an X-ray photon can be estimated.

A method of estimating the energy of a radiation quantum using equations will be described. It is assumed that the emission of radiation is performed upon a radiation imaging apparatus T times (T is a natural number greater than or equal to 2) and signals of T number of digital images are acquired from the radiation imaging apparatus. If the pixel value of a certain pixel in a t-th digital image (t is a natural number that is greater than or equal to 2 and is less than or equal to T) is I(t), the total number of radiation quanta that has reached and been absorbed by the pixel is set as N, and the energy of a radiation quantum is set as E, the following equation (1) is satisfied.

$$E \times N = \Sigma I(t) \quad (1)$$

If the arithmetic mean of the number of radiation quanta that has reached and been absorbed by the pixel in a single digital image is $n_{Ave}$, $n_{Ave}$ is represented by the following equation (2) using Equation (1).

$$n_{Ave} = N/T = \Sigma I(t)/E/T \quad (2)$$

If the sample variance of the number of radiation quanta that has reached and been absorbed by the pixel in a single digital image is $n_{Var}$, $n_{Var}$ is represented by the following equation (3) using Equation (1).

$$n_{Var} = [\{I(t)/E - n_{Ave}\}^2]/T \quad (3)$$

In the Poisson distribution, an expected value and a variance are equal to the parameter $\lambda$. With the increasing number of samples, an arithmetic mean gets closer to an expected value and a sample variance gets closer to a variance. By sufficiently (preferably infinitely) increasing the number of samples and making an approximation assuming that the arithmetic mean $n_{Ave}$ of the number of radiation quanta and the sample variance $n_{Var}$ of the number of radiation quanta are equal, the following equation (4) is derived under the assumption that Equations (2) and (3) are the same.

$$E=\Sigma\{I(t)^2\}/\Sigma\{I(t)\}-\{I(t)\}/T \qquad (4)$$

Thus, using the pixel value I(t) of the certain pixel in the t-th digital image, the energy E of a radiation quanta that has reached and been absorbed by the pixel can be estimated and calculated.

If the arithmetic mean of the pixel value I(t) is $I_{Ave}$, $I_{Ave}$ is represented by the following equation (5) using the arithmetic mean $n_{Ave}$ of the number of radiation quanta.

$$I_{Ave}=n_{Ave} \times E \qquad (5)$$

If the sample variance of pixel values is $I_{Var}$, $I_{Var}$ is represented by the following equation (6) using the sample variance $n_{Var}$ of the number of radiation quanta.

$$I_{Var}=n_{Var} \times E^2 \qquad (6)$$

The energy E of a radiation quantum that has reached and been absorbed by the pixel is therefore also represented by the following equation (7).

$$E=I_{Var}/I_{Ave}, \qquad (7)$$

The energy of a radiation quantum that reaches and is absorbed by the pixel is not constant in reality. For example, if a common X-ray generator generates X-rays at a tube voltage of 100 kV, X-ray photons of various energy less than or equal to 100 KeV can be generated. By making an approximation assuming that Equation (4) is satisfied even for such X-rays that is radiation, the average energy of radiation quanta that reaches and be absorbed by the pixel can be estimated. In addition, using the average energy of radiation quanta and the pixel value I(t) of a certain pixel in a t-th digital image in Equation (1), the number of radiation quanta can be estimated.

A method of estimating the average energy of radiation quanta under the assumption that a subject does not move has been described. However, in actual radiographic imaging, a subject sometimes moves while a plurality of images of the subject are captured (a digital image signal is acquired by a radiation imaging apparatus a plurality of times). For example, this occurs when the image of a moving organ such as the heart is captured or fluoroscopic imaging is performed during a surgical operation. In the case of the image capturing of a moving subject, the number of radiation quanta such as X-ray photons that reaches a certain pixel changes while a radiation imaging apparatus outputs data of a plurality of images. That is, the parameter λ for the Poisson distribution is changed. For example, as illustrated in FIG. 3A, it is assumed that an expected value of the number of radiation quanta is changed from 2 to 10 in a state where the energy of each radiation quantum is kept to 30 LSB. In this case, an expected pixel value becomes 180 LSB, the variance of a pixel value becomes 14,400 LSB, and the average energy E of radiation quanta estimated using Equation (7) becomes 80 LSB. That is, a large error arises between 30 LSB that is the actual energy of each radiation quantum and 80 LSB that is the average energy E of radiation quanta estimated using Equation (7). In an image generated with the average energy, an artifact occurs. This results in the reduction in a diagnostic capability.

In an embodiment of the present invention, for the estimation of the average energy of radiation quanta emitted to a predetermined pixel, the amount of temporal and/or spatial change in the pixel value of the pixel is used. The amount of temporal change in a pixel value means the difference between the pixel value of the predetermined pixel in a frame and the pixel value of a pixel corresponding to the predetermined pixel (a pixel at the same position as the predetermined pixel or in the vicinity of the predetermined pixel) in a different frame. The amount of spatial change in a pixel value means the difference between the pixel value of the predetermined pixel in a frame and the pixel value of a pixel next to or in the vicinity of the predetermined pixel in the frame. The amounts of temporal and spatial changes mean the mixture of the above-described amount of temporal change and the above-described amount of spatial change. The pixel value of the above-described predetermined pixel or the pixel value of a target pixel used to take a difference from the pixel value of the predetermined pixel may be provided in one or plurality. In a case where there is a plurality of pixels, a representative pixel value of these pixels (for example, a value obtained by performing recursive filter processing upon a predetermined pixel value or a value obtained by averaging processing) is used. The different frames used to obtain the amount of temporal change in a pixel value are preferably adjacent frames in a time axis, but may be apart from each other provided that the advantages of the present invention are not significantly reduced. The predetermined pixel and another pixel used to obtain the amount of spatial change in a pixel value are preferably next to each other, but may be apart from each other provided that the advantages of the present invention are not significantly reduced. A range in which the advantages of the present invention are not significantly reduced even if frames or pixels are apart from each other is regarded as a predetermined range including a portion of all pixels used for signal processing. Using this amount of change, it is possible to reduce an error in estimating the average energy of the predetermined pixel.

More specifically, in an embodiment of the present invention, the sample variance of pixel values is approximated by regarding it as one half times the square of the amount of temporal and/or spatial change in a predetermined pixel value. In a representative example, the sample variance of pixel values is approximated by regarding it as one half times the square of the difference between the pixel value of a predetermined pixel in a frame and the pixel value of a pixel at the same position as the predetermined pixel in a different frame.

Next, the energy E(t) of a radiation quantum at a predetermined pixel is considered on the basis of Equation (7). By replacing the arithmetic mean $I_A$, of the pixel values I(t) with the pixel value I(t) and replacing the sample variance $I_{Var}$ of pixel values with one half times the square of the difference between the pixel value and an adjacent pixel value, the following equation (8) is obtained.

$$E(t)=\{I(t)-I(t-1)\}^2/2I(t) \qquad (8)$$

In Equation (8), as the adjacent pixel value, the pixel value I(t−1) of a pixel in a digital image immediately before a digital image including the predetermined pixel is used. However, for example, as the adjacent pixel value, a pixel value I(t+1) of a pixel in a digital image immediately after the digital image including the predetermined pixel may also be used. In this case, Equation (9) is derived.

$$E(t)=[I(t)-\{I(t-1)+I(t+1)/2\}]^2/2I(t) \qquad (9)$$

That is, in a case where pixel values of pixels in digital images before and after the t-th digital image by U (U is greater than or equal to 2, and is much less than T) are used, Equations (10) and (11) are derived.

[Math.1]
$$E(t) = \left[I(t) - \frac{1}{U}\left\{\Sigma_{t-\frac{U+1}{2}}^{t-1} I(u) + \Sigma_{t+1}^{t+\frac{U-1}{2}} I(u)\right\}\right]^2 / 2I(t) \quad (10)$$

When U is an odd number, the following equation is derived.

[Math.2]
$$E(t) = \left[I(t) - \frac{1}{U}\left\{\Sigma_{t-\frac{U}{2}}^{t-1} I(u) + \Sigma_{t+1}^{t+\frac{U}{2}} I(u)\right\}\right]^2 / 2I(t) \quad (11)$$

That is, as represented by Equations (10) and (11), the energy E(t) of a radiation quantum at a predetermined pixel is obtained by dividing the square of the difference between a value including a predetermined pixel value and a value including another pixel value by a value including the predetermined pixel value.

The average energy $E_{Ave}$ of radiation quanta at a predetermined pixel is estimated using the energy E(t) of a radiation quantum at the predetermined pixel. For example, the average energy E of radiation quanta at a predetermined pixel is estimated using the energy E(t) of a radiation quantum at the predetermined pixel in the following equation (12).

$$E_{Ave} = \Sigma E(t)/T \quad (12)$$

That is, by averaging the energy E(t) of a radiation quantum at the predetermined pixel over a predetermined period, the average energy E of radiation quanta at the predetermined pixel is estimated. Using the estimated average energy E of radiation quanta at the predetermined pixel, an energy resolved radiographic image can be generated. That is, by performing the above-described estimation for all of a plurality of pixels, the average energy $E_{Ave}$ of radiation quanta at each of these pixels is estimated. On the basis of results of the estimations, an energy resolved radiographic image can be generated.

As illustrated in FIG. 3B, a large error occurs in the above-described energy E(t) of a radiation quantum at a predetermined pixel only when an expected value that is equal to the parameter λ for the Poisson distribution changes. Accordingly, using the above-described computation, the above-described artifact can be reduced.

It is desired that a calculation method of estimating the average energy E of radiation quanta at a predetermined pixel be changed when the energy E(t) of a radiation quantum at the predetermined pixel satisfies predetermined conditions. The predetermined conditions are, for example, a case where the energy E(t) of a radiation quantum at a predetermined pixel exceeds a predetermined threshold value Th as illustrated in FIG. 3B. For example, as illustrated in FIGS. 3A and 3B, it is assumed that the expected value of the number of radiation quanta changes at a $t_1$th image. In such a case, at the $t_1$th image, a large error may occur in energy $E(t_1)$ of a radiation quantum at a predetermined pixel. Accordingly, by determining whether the energy E(t) of a radiation quantum at a predetermined pixel exceeds a threshold value Th set in advance, the change in the parameter λ for the Poisson distribution can be detected. Subsequently, a sample variance and an arithmetic mean are obtained using pixel values in the range of t=0 to $t_{l-1}$, and a first average $E_1$ of energy of radiation quanta at the predetermined pixel is calculated using Equation (7). Next, a second average $E_2$ of energy of radiation quanta at the predetermined pixel is similarly calculated using pixel values in the range of $t=t_{l-1}$ to T−1. Using the following equation (13), the average energy $E_{Ave}$ of radiation quanta at the predetermined pixel is estimated.

$$E_{Ave} = \{E_1 \times t_{l-1} + E_2 \times (T-t_l-2)\}/(T-1) \quad (13)$$

That is, before and after the change in the parameter λ for the Poisson distribution, the average energy of radiation quanta at the predetermined pixel is calculated. Results of the calculation are then averaged. Thus, by calculating the average energy of radiation quanta before and after the estimation of energy of a radiation quantum at the predetermined pixel satisfying predetermined conditions and averaging results of the calculation, the average energy E of radiation quanta at the predetermined pixel is estimated. In an energy resolved radiographic image generated on the basis of the estimated average energy of radiation quanta at the predetermined pixel, the occurrence of an artifact caused by the change in an expected value can be further suppressed.

In a case where the energy E(t) of a radiation quantum at a predetermined pixel satisfies the above-described predetermined conditions, a method of exempting this pixel from a calculation target so as not to be used in Equation (11). Like in a case where Equation (11) is used, the occurrence of an artifact caused by the change in an expected value can be further reduced.

In the above description, the effect of noise of an electronic circuit included in, for example, an output circuit (system noise) and the effect of light scattering caused by a scintillator are ignored. In reality, however, a sample variance and a pixel value are affected by them in a radiation imaging apparatus. Instead of Equation (7), Equation (14) can be employed in which a represents the standard deviation of the value of noise (system noise) of an electronic circuit included in, for example, an output circuit and A represents a parameter representing light scattering in a scintillator.

$$E_{Ave} = A \times (I_{Var} - \sigma^2)/I_{Ave} \quad (14)$$

Equation (15) can be similarly employed instead of Equation (10), and Equation (16) can be similarly employed instead of Equation (11).

When U is an odd number, the following equation can be employed.

[Math.3]
$$E(t) = A \times \left[\left[I(t) - \frac{1}{U}\left\{\Sigma_{t-\frac{U+1}{2}}^{t-1} I(u) + \Sigma_{t+1}^{t+\frac{U-1}{2}} I(u)\right\}\right]^2/2 - \sigma^2\right]/I(t) \quad (15)$$

When U is an even number, the following equation can be employed.

[Math.4]

$$E(t) = A \times \left[\left[I(t) - \frac{1}{U}\left\{\sum_{t-\frac{U}{2}}^{t-1} I(u) + \sum_{t+1}^{t+\frac{U}{2}} I(u)\right\}\right]^2 / 2 - \sigma^2\right]/I(t) \quad (16)$$

Thus, by employing Equations (14) to (16), in an energy resolved radiographic image generated on the basis of the estimated energy of a radiation quantum at a predetermined pixel, the effects of system noise and light scattering caused by a fluorescent material can be reduced. In this embodiment, an indirect radiation imaging apparatus including a scintillator is used. However, a direct radiation imaging apparatus including, instead of a scintillator and a photoelectric conversion element, a conversion element made of a material (direct conversion material) such as CdTe with which radiation such as an X-ray can be directly converted into charges may be used. In this case, the above-described parameter A can represent the diffusion of charges by a direct conversion material. That is, the parameter A can be regarded as a signal transfer characteristic when radiation is converted into a signal. Here, σ and the parameter A can be individually used. In Equations (14) to (16), only one of them can be used.

In the above description, the time series of pixel values of a certain pixel included in a plurality of pixels is used. However, for example, a two-dimensional array with columns in the X axis and rows in the Y axis may be used (see, for example, FIG. 4). For example, at an edge part of a subject, the expected value of the number of radiation quanta reaching the part is not equal to that at the other part of the subject. In the edge part, the parameter k for the Poisson distribution is changed, and an artifact occurs. That is, in an embodiment of the present invention, a predetermined temporal and/or spatial range includes not only a predetermined range of a time-series of pixel values that are part of all acquired pixel values used for signal processing but also a predetermined range of the arrangement of pixels. In FIG. 4, pixel values in the X column direction are illustrated.

The energy E(n) of a radiation quantum at a predetermined pixel in a y-th row in an x column in a two-dimensional array is represented by, for example, the following equation (17) where I(x, y) represents a pixel value.

$$E(n) = [I(x,y) - \{I(x-1,y) + I(x,y-1) + I(x+1,y) + I(x,y+1)\}/4]^2 / 2I(x,y) \quad (17)$$

Equation (17) represents a case where among digital image signals obtained from a plurality of pixels in a matrix with X rows and Y columns, the pixel values of four adjacent pixels located above, below, to the left, or to the right of a predetermined pixel (x, y) are used. A single pixel located in an oblique direction with respect to the predetermined pixel may be additionally used. That is, the energy E(n) of a radiation quantum can be calculated by subtracting the pixel value of a predetermined pixel from the average of pixel values of pixels located in all directions with respect to the predetermined pixel, subtracting a result of the subtraction from the pixel value of the predetermined pixel, and dividing the square of a result of the subtraction by the pixel value of the predetermined pixel. By replacing a parameter for a time series with a parameter for a two-dimensional array in Equations (12) to (16), the energy E(n) of a radiation quantum at a predetermined pixel in the two-dimensional array and the average energy $E_{Ave}$ of radiation quanta at the predetermined pixel can be obtained.

A region for which the energy of a radiation quantum and the number of radiation quanta are estimated is not limited to a fixed shape. For example, a part of a digital image where the parameter λ for the Poisson distribution has changed may be set as a boundary and the digital image may be divided into a plurality of regions on the basis of the boundary. Energy and the number of radiation quanta in each of the regions may be estimated. In any of these cases, using the energy of a radiation quantum at a predetermined pixel, it is possible to suppress the occurrence of an artifact caused by the change in the parameter λ for the Poisson distribution.

A radiation imaging apparatus and a radiation imaging system which are suitable for the acquisition of pixel values used in an embodiment of the present invention will be described below.

First, a radiation imaging system will be described with reference to FIG. 5. FIG. 5 is a schematic block diagram of a radiation imaging system.

A radiation imaging system includes a radiation imaging apparatus 10, a control computer 13, a radiation control apparatus 12, and a radiation generation apparatus 11. The radiation imaging apparatus 10 includes a detection unit 101, a signal processing unit 105, a power supply unit 106, and a control unit 107. The detection unit 101 includes a pixel array 102 in which pixels for converting radiation or light into an electric signal are two-dimensionally arranged in a matrix, a driving circuit 103 for driving the pixel array 102, and an output circuit 104 for outputting an electric signal transmitted from the driven pixel array 102 as an image signal. An example of the detection unit 101 will be described in detail below with reference to FIGS. 6A and 6B.

The control computer 13 supplies a control signal to the radiation imaging apparatus 10 and the radiation control apparatus 12 on the basis of imaging information input by a photographer (not illustrated) via a control desk (not illustrated) of the control computer 13. Upon receiving a control signal from the control computer 13, the radiation control apparatus 12 controls the emission of radiation from a radiation source (not illustrated) in the radiation generation apparatus 11 and the operation of a collimator (not illustrated). Upon receiving a control signal from the control computer 13, the control unit 107 in the radiation imaging apparatus 10 controls each unit in the radiation imaging apparatus 10. In accordance with radiation emitted by the radiation generation apparatus 11 under the control of the radiation control apparatus 12, the detection unit 101 in the radiation imaging apparatus 10 outputs an image signal. The output image signal is subjected to image processing such as offset correction in the signal processing unit 105 and is then transmitted to the control computer 13 by known wire or wireless communication. The transmitted image signal is subjected to necessary image processing in the control computer 13 and is then displayed on a display unit (not illustrated) in the control computer 13.

Next, the detection unit 101 will be described with reference to FIGS. 6A, 6B, and 7. FIGS. 6A and 6B are schematic block diagrams of the detection unit 101 according to an embodiment of the present invention. FIG. 7 is a schematic equivalent circuit diagram of an exemplary single pixel of the detection unit 101.

In the pixel array 102, in order to acquire a pixel value in accordance with incident radiation, a plurality of pixels 20 for outputting an electric signal in accordance with radiation are arranged in preferably a two-dimensional array. As illustrated in FIG. 7, each of the pixels 20 includes a photoelectric conversion element 201 and a pixel circuit portion 202. The photoelectric conversion element 201 is an element for converting light, which has been converted by a scintillator from radiation, into charges. In this embodiment, as a photoelectric conversion element, a photodiode provided on a semiconductor substrate such as a silicon substrate is used. However, an amorphous silicon photoelectric conversion element provided on an insulating substrate such as a glass substrate or a conversion element for directly converting radiation into charges without using a scintillator may be used. The pixel circuit portion 202 is a circuit portion for amplifying charges from the photoelectric conversion element 201 and outputting the amplified charges as an electric signal, and the detailed exemplary configuration of the pixel circuit portion 202 will be described later.

A driving circuit portion 21 included in the driving circuit 103 is a circuit for operating the pixel array 102 in desired units of pixel groups by supplying a driving signal to the pixel array 102 via a driving wiring portion 24. In this embodiment, the driving circuit portion 21 operates the pixel circuit portions 202 in the pixels 20 in the pixel array 102 in units of rows. As the driving circuit portion 21, a shift register is preferably used. As each unit circuit portion 211, a unit circuit in the shift register can be used. The driving wiring portion 24 is a group of a plurality of driving lines prepared for individual driving signals. In this embodiment, the driving wiring portion 24 is provided for each row in the pixel array 102.

A reading circuit portion 23 included in the output circuit 104 is a circuit portion for converting electric signals output in parallel from the pixel array 102 via a signal line 25S and a signal line 25N into a series electric signal and reading the series electric signal. As illustrated in FIG. 6A, the reading circuit portion 23 includes a selection switch 231, a scanning circuit 22, an output line 232, and an output buffer 233. More specifically, as illustrated in FIG. 6B, the selection switch 231 includes a selection switch 231S, a selection switch 231N, a selection switch 231'S, and a selection switch 231'N. The output line 232 includes an output line 232S and an output line 232N. The output buffer 233 includes an output buffer 233S and an output buffer 233N. Here, S represents a component for an electric signal based on charges generated at a pixel in accordance with radiation, and N represents a component for an electric signal based on the offset of a pixel. The selection switch 231S and the selection switch 231N are provided for each column in the pixel array 102 and are elements for selecting a desired pixel column in the pixel array 102. Like in this embodiment, the pixel array 102 may be divided into a plurality of blocks, and the selection switches 231'S and 231'N for selecting one of the blocks may be disposed for each block. The scanning circuit 22 is a circuit for selecting one of the selection switches 231S and 231N as appropriate to convert electric signals output in parallel from the pixel array 102 into a series electric signal. As the scanning circuit 22 included in the output circuit 104, a shift register is preferably used. Like in this embodiment, a scanning circuit 22' for selecting one of the selection switches 231'S and 231'N as appropriate may be disposed for each block. The output line 232S and the output buffer 233S function as an output portion for outputting a series electric signal, and the output line 232N and the output buffer 233N also function as an output portion for outputting a series electric signal. The output lines 232S and 232N transmit a series electric signal, and the output buffers 233S and 233N perform buffer output of the transmitted series electric signal. The reading circuit portion 23 may further include a MOS 234S and a MOS 234N which are electrically connected to a signal line and are used as column buffers and current sources 235S and 235N.

The output circuit 104 further includes an A/D converter 26 that is electrically connected to the output line 232 via the output portion 26. The A/D converter 26 converts an analog signal based on an electric signal output from the pixel array 102 into a digital image signal DATA. The digital image signal DATA is transmitted to the signal processing unit 105 via a transmission line 27. A block 200 illustrated in FIG. 6A is a semiconductor chip in which components are integrated on a single semiconductor substrate. FIG. 6B is a block diagram used to describe the block 200 illustrated in FIG. 6A in more detail.

Next, an exemplary configuration of each of the pixels 20 will be described with reference to FIG. 7. FIG. 7 is a schematic equivalent circuit diagram of a single pixel in a radiation imaging apparatus. As described previously, the pixel 20 includes the photoelectric conversion element 201 and the pixel circuit portion 202. The photoelectric conversion element 201 is typically a photodiode. The pixel circuit portion 202 includes an amplification circuit portion 204, a clamping circuit portion 206, a sample-and-hold circuit portion 207, and a selection circuit portion 208.

The photoelectric conversion element 201 includes a charge storage portion. The charge storage portion is connected to the gate of a MOS transistor 204a in the amplification circuit portion 204. The source of the MOS transistor 204a is connected to a current source 204c via a MOS transistor 204b. The MOS transistor 204a and the current source 204c form a source follower circuit. The MOS transistor 204b is an enable switch that is turned on and operates the source follower circuit when an enable signal EN supplied to its gate is set to an active level.

In an example illustrated in FIG. 7, the charge storage portion in the photoelectric conversion element 201 and the gate of the MOS transistor 204a form a common node, and this node functions as a charge-to-voltage conversion portion for converting charges stored in the charge storage portion into a voltage. That is, in the charge-to-voltage conversion portion, a voltage V (=Q/C) that is determined in accordance with charges Q stored in the charge storage portion and a capacitance value C of the charge-to-voltage conversion portion occurs. The charge-to-voltage conversion portion is connected to a reset potential Vres via a reset switch 203. When a reset signal PRES is set to an active level, the reset switch 203 is turned on and the potential of the charge-to-voltage conversion portion is reset to the reset potential Vres.

The clamping circuit portion 206 clamps noise output from the amplification circuit portion 204 in accordance with the potential of the reset charge-to-voltage conversion portion using a clamp capacitor 206a. That is, the clamping circuit portion 206 is a circuit for removing this noise from a signal output from the source follower circuit in accordance with charges generated by photoelectric conversion in the photoelectric conversion element 201. This noise includes kTC noise generated at the time of reset. Clamping is performed by setting a clamp signal PCL to an active level to turn on a MOS transistor 206b and then setting the clamp signal PCL to an inactive level to turn off the MOS transistor 206b. An output terminal of the clamp capacitor 206a is connected to the gate of a MOS transistor 206c. The source of the MOS transistor 206c is connected to a current source 206e via a MOS transistor 206d. The MOS transistor 206c and the current source 206e form a source follower circuit. The MOS transistor 206d is an enable switch that is turned on and operates the source follower circuit when an enable signal $EN_0$ supplied to its gate is set to an active level.

A signal output from the clamping circuit portion 206 in accordance with charges generated by photoelectric conversion in the photoelectric conversion element 201 is written in a capacitor 207Sb via a switch 207Sa as an optical signal when an optical signal sampling signal TS is set to an active level. A signal output from the clamping circuit portion 206 when the MOS transistor 206b is turned on immediately after the potential of the charge-to-voltage conversion portion has been reset is noise. This noise is written in a capacitor 207Nb via a switch 207Na when a noise sampling signal TN is set to an active level. This noise includes the offset component of the clamping circuit portion 206. The switch 207Sa and the capacitor 207Sb form a signal sample-and-hold circuit 207S. The switch 207Na and the capacitor 207Nb form a noise sample-and-hold circuit 207N. The sample-and-hold circuit portion 207 includes the signal sampleand-hold circuit 207S and the noise sample-and-hold circuit 207N.

When the driving circuit portion 21 sets a row selection signal VST to an active level, signal (optical signal) stored in the capacitor 207Sb is output to the signal line 25S via a MOS transistor 208Sa and a row selection switch 208Sb. At the same time, a signal (noise) stored in the capacitor 207Nb is output to the signal line 25N via a MOS transistor 208Na and a row selection switch 208Nb. The MOS transistor 208Sa forms a source follower circuit along with the constant current source 235S (see FIG. 6B) provided at the signal line 25S. The MOS transistor 208Na similarly forms a source follower circuit along with the constant current source 235N (see FIG. 6B) provided at the signal line 25N. The MOS transistor 208Sa and the row selection switch 208Sb form a signal selection circuit portion 208S. The MOS transistor 208Na and the row selection switch 208Nb form a noise selection circuit portion 208N. The selection circuit portion 208 includes the signal selection circuit portion 208S and the noise selection circuit portion 208N.

The pixel 20 may include an addition switch 209S for adding optical signals obtained in the pixels 20 adjacent to each other. In an addition mode, an addition mode signal ADD is set to an active level, so that the addition switch 209S is brought into an ON state. As a result, the capacitors 207Sb in the adjacent pixels 20 are interconnected with the addition switches 209S and optical signals are averaged. The pixel 20 similarly includes an addition switch 209N for adding noises in the pixels 20 adjacent to each other. When the addition switch 209N is turned on, the capacitors 207Nb in the adjacent pixels 20 are interconnected with the addition switches 209N and noises are averaged. An addition portion 209 includes the addition switch 209S and the addition switch 209N.

The pixel 20 may include a sensitivity change portion 205 for changing sensitivity. For example, the pixel 20 may include a first sensitivity change switch 205a, a second sensitivity change switch 205'a, and circuit elements for these switches. When a first change signal WIDE is set to an active level, the first sensitivity change switch 205a is turned on and the capacitance value of a first additional capacitor 205b is added to the capacitance value of the charge-to-voltage conversion portion. As a result, the sensitivity of the pixel 20 decreases. When a second change signal WIDE2 is set to an active level, the second sensitivity change switch 205'a is turned on and the capacitance value of a second additional capacitor 205'b is added to the capacitance value of the charge-to-voltage conversion portion. As a result, the sensitivity of the pixel 20 is further decreases. By adding a function of reducing the sensitivity of the pixel 20, the amount of light received by the pixel 20 can be increased and a dynamic range can be increased. In a case where the first change signal WIDE is set to an active level, an enable signal $EN_n$ may be set to an active level to cause not only the MOS transistor 204a but also the MOS transistor 204'a to perform a source follower operation.

Next, an exemplary pixel value acquisition operation of a radiation imaging apparatus will be described with reference to FIG. 8. FIG. 8 is a timing chart describing an exemplary operation of a radiation imaging apparatus.

Upon receiving a synchronizing signal SYNC from the radiation control apparatus 12 via the control computer 13, the control unit 107 in the radiation imaging apparatus 10 causes the detection unit 101 to perform reset driving RD. In accordance with the synchronizing signal SYNC, an imaging interval FT and a frame rate are determined. In the reset driving RD, in response to the synchronizing signal SYNC, a reset operation of resetting the photoelectric conversion element 201 and an operation of storing a voltage corresponding to the kTC noise in the clamp capacitor 206a are performed. The control unit 107 sets the enable signal EN to an active level (H) to bring the MOS transistors 204b and 206d into conduction, so that the MOS transistors 204a and 206c are ready to perform a source follower operation. While the enable signal EN is at H, the control unit 107 sets the reset signal PRES to an active level (H) to bring the MOS transistor 204a into conduction. As a result, the reset operation of connecting the photoelectric conversion element 201 to the reset voltage VRES and resetting the photoelectric conversion element 201 is performed. A voltage based on the gate voltage of the MOS transistor 204a at the time of reset is supplied to one terminal of the clamp capacitor 206a. Subsequently, the control unit 107 sets the reset signal PRES to an inactive level (L) and then sets the clamp signal PCL to an active level to bring the MOS transistor 206b into conduction, so that a clamp voltage VCL is supplied to the other terminal of the clamping circuit portion 206. After that, the control unit 107 sets the clamp signal PCL to the inactive level (L) to bring the MOS transistor 206b into an OFF state. As a result, a clamping operation of storing charges based on the potential difference between one terminal and the other terminal of the clamping circuit portion 206 in the clamping circuit portion 206 and clamping the kTC noise caused by, for example, the heat of the MOS transistor 204b is performed. Subsequently, the control unit 107 sets the enable signal EN to L to bring the MOS transistors 204b and 206d out of conduction. The MOS transistors 204b and 206d are brought into a non-operating state, and the reset driving ends. The reset driving RD is performed upon all of the pixels 20 at the same time to prevent the difference in control timing. As a result, data continuity can be achieved between adjacent pixels.

In synchronization with the synchronizing signal SYNC transmitted from the radiation control apparatus 12, the radiation generation apparatus 11 emits radiation to the radiation imaging apparatus 10, so that charges are generated in the photoelectric conversion element 201 in accordance with the incident radiation. The control unit 107 causes the sampling driving SD to the detection unit 101. In the sampling driving SD, a signal based on the charges generated in the photoelectric conversion element 201 in accordance with the radiation is sampled as an optical signal and is then stored in the capacitor 207Sb in the sample-and-hold circuit portion 207. In addition, in the sampling driving SD, noise corresponding to fixed pattern noise due to, for example, manufacturing variations among elements is sampled as a noise signal and is then stored in the capacitor 207Nb. The control unit 107 sets the enable signal EN to the active level (H) to bring the MOS transistors 204b and 206d into conduction, so that the MOS transistors 204b and 206c are ready to perform a source follower operation. While the enable signal EN is at H, the control unit 107 sets the optical signal sampling signal TS to the active level (H). As a result, a signal output from the clamping circuit portion 206 in accordance with charges generated by photoelectric conversion in the photoelectric conversion element 201 is written in the capacitor 207Sb via the switch 207Sa. When the control unit 107 sets the optical signal sampling signal TS to the inactive level (L), the written signal is stored in the capacitor 207Sb. Subsequently, the control unit 107 sets the clamp signal PCL to an active level to bring the MOS transistor 206b into conduction, so that the clamp voltage VCL is supplied to the other terminal of the clamping circuit portion 206. While the clamp signal PCL is at the active level, the control unit 107 sets the noise sampling signal TN to an active level, so that a noise signal is written in the capacitor 207Nb. When the control unit 107 sets the noise sampling signal TN to the inactive level (L), the noise signal is stored in the capacitor 207Nb. Subsequently, while the clamp signal PCL is at the active level, the control unit 107 sets the reset signal PRES to the active level (H) to bring the MOS transistor 204a into conduction. When the control unit 107 sets the reset signal PRES to the inactive level (L) and then sets the clamp signal PCL to an inactive level, the reset operation and the clamping operation, which have been described in the reset driving, are performed. Subsequently, the control unit 107 sets the enable signal EN to L to bring the MOS transistors 204b and 206d into conduction. As a result, the MOS transistors 204b and 206d are brought into a non-operating state, and the sampling driving SD ends. The sampling driving SD is performed upon all of the pixels 20 at the same time to prevent the difference in control timing. As a result, data continuity can be achieved between adjacent pixels.

Subsequently, the control unit 107 performs scanning driving to scan the pixel array 102. After the sampling driving SD has ended, the driving circuit portion 21 sets the selection signal VST (VST0) for the first row to an active level. This means that the driving circuit portion 21 selects the first row in the pixel array 102. In this state, the scanning circuit 22 sequentially sets column selection signals HST (HST0 to HSTn) for the first column to the last column to an active level. This means that the scanning circuit 22 sequentially selects the first column to the last column in the pixel array 102. As a result, optical signals of pixels in the first column to the last column in the first row in the pixel array 102 are output from the output buffer 233S, and noise of pixels in the first column to the last column in the first row in the pixel array 102 are output from the output buffer 233N. Subsequently, the driving circuit portion 21 sets the selection signal VST (VST1) for the second row to an active level. In this state, unit circuit portions in the scanning circuit 22 corresponding to the first column to the last column set the column selection signals HST (HST0 to HSTn) to an active level, respectively. By performing such an operation upon from the first row to the last row, electric signals output in parallel from the pixel array 102 are converted into a series electric signal and is then read by the reading circuit portion 23. The read electric signal is converted into a digital image signal by the A/D converter 26. Thus, the radiation imaging apparatus 10 acquires a single digital image signal.

When the control unit 107 periodically repeats the reset driving RD, the sampling driving SD, and the scanning driving, the detection unit 101 acquires a plurality of digital image signals. Using the pixel value of a predetermined pixel included in the acquired digital image signals, the signal processing unit 105 can perform processing according to an embodiment of the present invention.

It is desired that the above-described processing be performed using a program. However, the processing may be performed in whole or in part using a circuit. The above-described processing may be performed not by the signal processing unit 105 but by the control computer 13 or by both the signal processing unit 105 and the control computer 13. That is, a signal processor according to an embodiment of the present invention and a radiographic image signal processing apparatus according to an embodiment of the present invention correspond to at least one of the signal processing unit 105, the control computer 13, and the combination of the signal processing unit 105 and the control computer 13.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-214987, filed Oct. 30, 2015, which is hereby incorporated by reference herein in its entirety.

REFERENCE SIGNS LIST

20 Pixel
105 Signal processing unit
The invention claimed is:
1. A radiation imaging system comprising:
   a detector including a plurality of pixels from which pixel values based on incident radiation are acquired; and
   a signal processor configured to perform signal processing to generate an energy resolved radiographic image on the basis of an amount of change in a pixel value of a predetermined pixel included in the plurality of pixels, wherein the signal processor generates, in a predetermined temporal and/or spatial range including a pixel value of the predetermined pixel that is part of all pixel values used for the signal processing, the energy resolved radiographic image using, as the amount of change in the pixel value of the predetermined pixel, a square of a difference between a value including the predetermined pixel value and a value including another pixel value included in the predetermined temporal and/or spatial range.

2. The radiation imaging system according to claim 1, wherein the signal processor estimates energy of a radiation quantum of the radiation at the predetermined pixel using an amount of change in a pixel value of the predetermined pixel, and estimates average energy of radiation quanta at the predetermined pixel on the basis of the estimated energy at the predetermined pixel.

3. The radiation imaging system according to claim 2, wherein the signal processor generates the energy resolved radiographic image on the basis of the average energy of radiation quanta at the predetermined pixel.

4. The radiation imaging system according to claim 3, wherein the energy of a radiation quantum at the predetermined pixel is estimated using a square of a difference between a value including the predetermined pixel value and a value including another pixel value included in the predetermined temporal and/or spatial range.

5. The radiation imaging system according to claim 4, wherein the energy of a radiation quantum at the predetermined pixel is estimated by dividing one half times a square of a difference between a value including the predetermined pixel value and a value including the other pixel value by the value including the predetermined pixel value.

6. The radiation imaging system according to claim 3, wherein the signal processor generates the energy resolved radiographic image using the average energy of radiation quanta at the predetermined pixel which is estimated by averaging energy of radiation quanta at the predetermined pixel in the predetermined temporal and/or spatial range.

7. The radiation imaging system according to claim 6, wherein, in a case where the energy of a radiation quantum at the predetermined pixel satisfies predetermined conditions, the energy at the predetermined pixel is not used for calculation of the average energy.

8. The radiation imaging system according to claim 6, wherein, in a case where the energy of a radiation quantum at the predetermined pixel satisfies predetermined conditions, a calculation method of estimating the average energy of radiation quanta at the predetermined pixel is changed.

9. The radiation imaging system according to claim 8, wherein, in a case where the energy of a radiation quantum at the predetermined pixel satisfies predetermined conditions, the average energy of radiation quanta at the predetermined pixel is estimated by averaging energy of radiation quanta at pixels calculated before and after estimation of energy of a radiation quantum at the predetermined pixel.

10. The radiation imaging system according to claim 2, wherein the predetermined temporal and/or spatial range includes a predetermined range of a time-series of pixel values of the predetermined pixel in a case where an image signal based on pixel values of the pixels is acquired a plurality of times.

11. The radiation imaging system according to claim 10, wherein the value including the other pixel value is a value including a pixel value adjacent to the predetermined pixel value in the time-series of pixel values of the predetermined pixel.

12. The radiation imaging system according to claim 2, wherein the predetermined temporal and/or spatial range includes a predetermined range of arrangement of the pixels.

13. The radiation imaging system according to claim 12, wherein the value including the other pixel value is a value including a pixel value of a pixel adjacent to the predetermined pixel.

14. The radiation imaging system according to claim 2, wherein the detector includes an output circuit configured to output signals based on the radiation from the pixels to obtain the pixel values, and wherein, for estimation of the energy of a radiation quantum at the predetermined pixel, a noise value of an electronic circuit including the output circuit is also used.

15. The radiation imaging system according to claim 2, wherein, for estimation of the energy of a radiation quantum at the predetermined pixel, a parameter is also used which represents signal transmission characteristics when the pixels convert the radiation into signals based on the radiation to obtain the pixel values.

16. The radiation imaging system according to claim 1, wherein the pixels include a scintillator configured to convert the radiation into light and a plurality of photoelectric conversion elements configured to convert the light into charges.

17. A signal processing apparatus, wherein the signal processing apparatus performs signal processing to generate an energy resolved radiographic image on the basis of an amount of change in a pixel value of a predetermined pixel included in a plurality of pixels from which pixel values based on incident radiation are acquired, wherein the signal processing apparatus generates, in a predetermined temporal and/or spatial range including a pixel value of the predetermined pixel that is part of all pixel values used for the signal processing, the energy resolved radiographic image using, as the amount of change in the pixel value of the predetermined pixel, a square of a difference between a value including the predetermined pixel value and a value including another pixel value included in the predetermined temporal and/or spatial range.

18. A signal processing method comprising performing signal processing for generating an energy resolve radiographic image on the basis of an amount of change in a pixel value of a predetermined pixel included in the pixels, wherein the energy resolved radiographic image is generated, in a predetermined temporal and/or spatial range including a pixel value of the predetermined pixel that is part of all pixel values used for the signal processing, using, as the amount of change in the pixel value of the predetermined pixel, a square of a difference between a value including the predetermined pixel value and a value including another pixel value included in the predetermined temporal and/or spatial range.

* * * * *